United States Patent [19]
Vanmechelen et al.

[11] Patent Number: 6,121,003
[45] Date of Patent: *Sep. 19, 2000

[54] MONOCLONAL ANTIBODIES SPECIFIC FOR AN EPITOPE OF PHOSPHORYLATED TAU, AND THEIR USE

[75] Inventors: Eugeen Vanmechelen, Nazareth-Eke; Andre Van De Voorde, Lokeren, both of Belgium

[73] Assignee: Innogentics N.V., Gent, Belgium

[ * ] Notice: This patent issued on a continued prosecution application filed under 37 CFR 1.53(d), and is subject to the twenty year patent term provisions of 35 U.S.C. 154(a)(2).

[21] Appl. No.: 08/776,404
[22] PCT Filed: Jul. 31, 1995
[86] PCT No.: PCT/EP95/03032
   § 371 Date: Mar. 24, 1997
   § 102(e) Date: Mar. 24, 1997
[87] PCT Pub. No.: WO96/04309
   PCT Pub. Date: Feb. 15, 1996

[30] Foreign Application Priority Data

Jul. 29, 1994 [EP] European Pat. Off. ............... 94870131

[51] Int. Cl.$^7$ .......................... G01N 33/53; C07K 16/00; C12P 21/08
[52] U.S. Cl. .......................... 435/7.1; 435/7.92; 435/331; 435/975; 436/547; 436/548; 436/811; 436/503; 530/387.9; 530/388.1
[58] Field of Search .............................. 530/387.1, 387.9, 530/388.1, 389.1; 435/7.1, 7.92, 7.93, 7.94, 7.95, 70.1, 70.21, 326, 960, 331, 975; 436/501, 503, 518, 524, 528, 811, 547, 548

[56] References Cited

FOREIGN PATENT DOCUMENTS

| | | |
|---|---|---|
| 1 302 250 | 6/1992 | Canada . |
| 0 544 942 | 6/1993 | European Pat. Off. . |
| 0 616 032 | 9/1994 | European Pat. Off. . |
| WO89/03993 | 5/1989 | WIPO . |
| WO93/08302 | 4/1993 | WIPO . |
| WO93/11231 | 6/1993 | WIPO . |
| WO94/13795 | 6/1995 | WIPO . |
| WO95/17429 | 6/1995 | WIPO . |

OTHER PUBLICATIONS

Harlow et al, "Antibodies A Laboratory Manual", Cold Spring Harbor Laboratory 1988, pp. 274–275.

Mercken et al., "Monoclonal Antibodies with Selective Specificity for Alzheimer Tau are Directed Against Phosphate–Sensitive Epitopes," pp. 265–272, Acta Neuropathologica, vol. 84, No. 6, Berlin, Germany (1992).

Drewes et al., "Mitogen Activated Protein (MAP) Kinase Transforms Tau Protein into Alzheimer–like State," pp. 2131–2138, The EMBO Journal, vol. 11, No. 6, Oxford, England (Jun. 1992).

Roder et. al., "Brain Protein Kinase PK40erk Converts Tau into a PHF–like Form as Found in Alzheimer's Disease," pp. 639–647, Biochemical and Biophysical Research Communications, vol. 193, No. 2, Duluth, Minnesota (Jun. 15, 1993).

Hanger et al., "Glycogen Synthase Kinase–3 Induces Alzheimer's Disease–like Phosphorylation of Tau: Generation of Paired Helical Filament Epitopes and Neuronical Localization of the Kinase," pp. 58–62, Neuroscience Letters, vol. 147, No. 1, Shannon, Ireland (Nov. 23, 1992).

Vandermeeren et al., "Detection of Tau Proteins in Normal and Alzheimer's Disease Cerebrospinal Fluid with a Sensitive Sandwich Enzyme–linked Immunosorbent Assay," pp. 1828–1834, Journal of Neurochemistry, vol.61, No. 8, New York, New York (Nov. 1993).

Lichtenberg–Kragg et al., "Phosphorylation–dependent Epitopes of Neurofilament Anitbodies on Tau Protein and Relationship with Alzheimer Tau," pp. 5384–5388, Proceedings of the National Academy of Sciences of the USA, vol. 89, No. 12, Washington, DC (Jun. 1992).

*Primary Examiner*—Patricia A. Duffy
*Attorney, Agent, or Firm*—Howrey Simon Arnold & White, LLP

[57] ABSTRACT

The present invention relates to a monoclonal antibody which forms an immunological complex with a phosphorylated epitope of a particular subclass or form of phosphorylated tau protein without forming an immunological complex with (i) fetal tau or (ii) biopsy or autopsy derived brain material from patients having died or suffering from diseases in which neurofibrillary tangle (NFT) is not a pathological hallmark. The invention also relates to a process for diagnosing brain diseases involving monoclonal antibodies of the invention. The invention also relates to a region of the tau molecule which is specifically recognized by the monoclonal antibodies of the invention.

19 Claims, No Drawings

```
                          SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 1:

Asp Gly Lys Thr Lys Ile Ala Thr Pro Arg Gly Ala Ala Pro Pro Gly
1               5                   10                  15

Gln Lys Gly Gln Ala Asn Ala Thr Arg Ile Pro Ala Lys Thr Pro Pro
                20                  25                  30

Ala Pro Lys Thr Pro Pro Ser Ser Gly Glu Pro Pro Lys Ser Gly Asp
            35                  40                  45

Arg Ser Gly Tyr Ser Ser Pro Gly Ser Pro Gly Thr Pro Gly Ser Arg
    50                  55                  60

Ser Arg Thr Pro Ser Leu Pro Thr Pro Pro Thr Arg Glu Pro Lys Lys
65                  70                  75                  80

Val Ala Val Val Arg Thr Pro Pro Lys Ser Pro Ser Ser Ala Lys Ser
                85                  90                  95

Arg Leu Gln Thr Ala Pro Val Pro Met Pro
                100                 105

(2) INFORMATION FOR SEQ ID NO: 2:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
```

-continued

```
            (A) NAME/KEY: Modified-site
            (B) LOCATION: 7
            (D) OTHER INFORMATION: /note= "Xaa is Lys, Gly or Leu"

(xi) SEQUENCE DESCRIPTION: SEQ ID NO: 2:

Asn Asn Asn Asn Gly Thr Xaa Ile Gly
1               5

(2) INFORMATION FOR SEQ ID NO: 3:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Xaa is Asn, Gly, Ala or Pro"

(ix) FEATURE:
        (A) NAME/KEY: Modified-site
        (B) LOCATION: 3
        (D) OTHER INFORMATION: /note= "Xaa is Ile, Lys, Ala or Arg"

(ix) FEATURE:
        (A) NAME/KEY: Modified-site
        (B) LOCATION: 4
        (D) OTHER INFORMATION: /note= "Xaa is Arg, Asn, Val or Lys"

(ix) FEATURE:
        (A) NAME/KEY: Modified-site
        (B) LOCATION: 5
        (D) OTHER INFORMATION: /note= "Xaa is Arg, Val, His or Gly"

(ix) FEATURE:
        (A) NAME/KEY: Modified-site
        (B) LOCATION: 6
        (D) OTHER INFORMATION: /note= "Xaa is Ile or His"

(ix) FEATURE:
        (A) NAME/KEY: Modified-site
        (B) LOCATION: 7
        (D) OTHER INFORMATION: /note= "Xaa is Pro or Ala"

(xi) SEQUENCE DESCRIPTION: SEQ ID NO: 3:

Asp Xaa Xaa Xaa Xaa Xaa Xaa Ala
1               5

(2) INFORMATION FOR SEQ ID NO: 4:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Xaa is Gly or Ser"

(ix) FEATURE:
        (A) NAME/KEY: Modified-site
        (B) LOCATION: 3
        (D) OTHER INFORMATION: /note= "Xaa is Thr, Pro or Lys"

(ix) FEATURE:
        (A) NAME/KEY: Modified-site
        (B) LOCATION: 4
```

```
            (D) OTHER INFORMATION: /note= "Xaa is Arg or Glu"

(ix) FEATURE:
            (A) NAME/KEY: Modified-site
            (B) LOCATION: 6
            (D) OTHER INFORMATION: /note= "Xaa is Ile or Ala"

(ix) FEATURE:
            (A) NAME/KEY: Modified-site
            (B) LOCATION: 7
            (D) OTHER INFORMATION: /note= "Xaa is Ala or Ser"

(ix) FEATURE:
            (A) NAME/KEY: Modified-site
            (B) LOCATION: 8
            (D) OTHER INFORMATION: /note= "Xaa is Gly, Thr or Leu"

(xi) SEQUENCE DESCRIPTION: SEQ ID NO: 4:

Asp Xaa Xaa Xaa Val Xaa Xaa Xaa Val Ser Xaa Xaa Lys Gly Gly
1               5                   10                  15

(2) INFORMATION FOR SEQ ID NO: 5:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /note= "Xaa is Pro or Glu"

(ix) FEATURE:
            (A) NAME/KEY: Modified-site
            (B) LOCATION: 4
            (D) OTHER INFORMATION: /note= "Xaa is Glu or Arg"

(ix) FEATURE:
            (A) NAME/KEY: Modified-site
            (B) LOCATION: 5
            (D) OTHER INFORMATION: /note= "Xaa is Gln, Ala or Leu"

(xi) SEQUENCE DESCRIPTION: SEQ ID NO: 5:

Asp Gly Xaa Xaa Xaa Xaa Asp
1               5
```

MONOCLONAL ANTIBODIES SPECIFIC FOR AN EPITOPE OF PHOSPHORYLATED TAU, AND THEIR USE

FIELD OF THE INVENTION

The present invention relates to the field of diagnosis of Alzheimer's disease.

The invention relates to new monoclonal antibodies specific for a particular type of phosphorylated epitopes present in a particular form or subclass of phosphorylated tau, to the hybridomas secreting these monoclonal antibodies, and to the antigen recognition pattern of these monoclonal antibodies and their applications. The invention also relates to a process for diagnosing brain diseases involving the monoclonal antibodies of the invention, more particularly in brain and body fluid such as cerebrospinal fluid (CSF). The invention also relates to a region of the tau molecule modifiable in vivo by the process of phosphorylation, which is found to be associated with the formation of "neurofibrillary tangles" (NFT) and "paired helical filaments" (PHF) as they occur in several types of dementia and which is specifically recognized by the monoclonal antibodies of the invention.

BACKGROUND OF THE INVENTION

Alzheimer's disease (AD) is the most common form of adult-onset dementia. At present, no reliable biochemical test is available for antemortem diagnosis of AD. The disease is usually diagnosed clinically on the basis of exclusion of other forms of dementia. The diagnosis can only be confirmed irrevocably by neuropathologic examination and the demonstration of large amounts of neuritic (senile) plaques and neurofibrillary tangles (NFT) in particular brain regions (McKhann et al, 1984), the latter appearing to correlate better with the severity and the duration of AD.

Neurofibrillary tangles consist of paired helical filaments (PHF). The microtubule-associated protein tau is a major protein component of PHF and NFT (Brion et al., 1985b; Delacourte and Defossez, 1986; Grundke-Iqbal et al., 1986; Kosik et al., 1986; Wood et al., 1986; Kondo et al., 1988).

Tau protein exists in different isoforms, of which 4 to 6 are found in adult brain but only 1 isoform is detected in fetal brain. The diversity of the isoforms is generated from a single gene on human chromosome 17 by alternative mRNA splicing (Himmler, 1989; Goedert et al., 1989; Andreadis et al., 1992). The most striking feature of tau protein, as deduced from molecular cloning, is a stretch of 31 or 32 amino acids, occurring in the carboxy-terminal part of the molecule, which can be repeated either 3 or 4 times. Additional diversity is generated through 29 or 58 amino acid-long insertions in the $NH_2$-terminal part of tau molecules (Goedert et al., 1989). For simplicity, all numbering in this patent application refers to the human tau variant htau40 containing all exons (441 amino acids long) according to Goedert et al (1989).

In vivo tau promotes microtubule assembly and stability in the axonal compartment of neurons by interactions involving its microtubule binding domain which is localized in the repeat region of tau (255–381) (Lewis et al, 1990).

In normal circumstances adult brain contains 2 à 3 mol phosphate per mole of tau (Selden and Pollard, 1983; Ksiezak-Reding et al, 1992). Phosphorylation of different sites in normal tau as studied in rat and humans is dependent on the developmental state (Lee et al, 1991; Bramblett et al, 1993; Goedert et al, 1993a). Tau variants of 60, 64 and 68 kDa arising as a consequence of phosphorylation have been detected in brain areas showing neurofibrillary tangles (Delacourte et al, 1990; Goedert et al., 1992; Flament et al., 1990b, Greenberg & Davies, 1990). In tau isolated from PHF (PHF-tau), phosphorylation can occur at several positions (Iqbal et al., 1989; Lee et al., 1991; Hasegawa et al., 1992).

Sofar, the detection of PHF-tau in brain extracts, either via antibodies (Mab Alz50: Ghanbari et al., 1990; Mab Ab423: Harrington et al., 1991; Mab AT120: Vandermeeren et al., 1993; Mab AT180; Mab AT270: International application No. PCT/EP 94/04146 filed on Dec. 14, 1994 and Mab AT8: International application published under WO 93/08302), or via the change in molecular weight (Flament et al., 1990, Delacourte et al., 1993), or else by functional assay (Bramblett et al., 1992) has been used to discriminate dementia with altered cytoskeletal properties from normal aged subjects or from patients with other types of dementia. A combination of monoclonal antibodies each-recognizing non-phosphorylated epitopes of tau has been used to detect the presence of tau and PHF-tau in CSF (Van de Voorde et al., 1995). However, this assay lacks the necessary discriminative power to distinguish AD patients from patients suffering from other neurodegenerative disorders.

AIMS OF THE INVENTION

The aim of the present invention is to provide monoclonal antibodies which allow the sensitive detection of a particular form or a particular subclass of phosphorylated tau present in freshly isolated brains of patients having died from Alzheimer's disease. Said particular form or subclass of phosphorylated tau is indicative for AD and is distinct from other phosphorylated tau variants which can be demonstrated by the use of monoclonal antibodies such as Tau1, AT8, T3P, PHF1, AT180, AT270 (Kosik et al., 1988; Trojanowski et al., 1989, Lee et al., 1991; Goedert et al., 1994; Mercken et al., 1992,; Binder et al., 1985; Greenberg & Davies, 1990; International application No. PCT/EP 94/04146 filed on Dec. 14, 1994; International application published under WO 93/08302).

The invention also aims at providing the hybridomas which secrete the above-said monoclonal antibodies.

The invention furthermore aims at providing the epitopes of the phosphorylated tau protein present in brain homogenates or in body fluids such as cerebrospinal fluid, which are specifically recognized by said monoclonal antibodies.

The invention also aims at providing a process for the detection or diagnosis in vitro of brain diseases detected by means of these monoclonal antibodies.

Finally, the present invention aims at providing kinases or phosphorylases responsible for the phosphorylation or the dephosphorylation of the epitopes recognized by the monoclonal antibodies of the present invention.

The present invention also aims at a process for the detection in vitro of substances which are capable to interfere with the kinases or the phosphorylases which are implicated in the phosphorylation or the dephosphorylation of the epitopes recognized by the monoclonal antibodies of the present invention.

SUMMARY OF THE INVENTION

The present invention relates to the new and surprising finding that adult human tau isolated from fresh surgical biopsy samples of Alzheimer patients is phosphorylated at a particular site different from those previously designated as "abnormally phosphorylated" or "PHF-tau", since this site could not be detected in autopsy-derived adult human tau from normal individuals or from non-AD patients.

Previously, PHF-tau or AD-tau was thought to be phosphorylated at unique sites ("abnormal phosphorylation"), different from the "normal" phosphorylation as found in adult tau of non-AD patients. The present invention discloses the finding that several of these previously designated "abnormally phosphorylated" sites also occur in fresh biopsy-derived tau from non-AD patients. The monoclonal antibodies of the invention (similar to AT100), however, are capable of detecting a phosphorylation site that is unique to PHF-tau from the AD brain and that does not detect any of the fresh biopsy- or autopsy-derived brain tau preparations from normal individuals or non-AD patients.

All previously identified monoclonal antibodies that react with PHF-tau appear to be not truly PHF-tau specific when tested upon fresh biopsy-derived and fetal samples from normal individuals or non-AD patients. The monoclonal antibodies of the present invention are thus said to detect only a subset of phosphorylated tau proteins which are truly indicative of AD in fresh biopsy samples.

DETAILED DESCRIPTION OF THE INVENTION

The present invention relates more particularly to a monoclonal antibody which forms an immunological complex with a phosphorylated epitope present in a particular form or subclass of phosphorylated tau and which does not form such an immunological complex with (i) fetal tau or (ii) tau isolated from biopsy- or autopsy-derived brain material from the brains of patients having died or suffering from diseases in which the occurrence of NFT is not a pathological hallmark (also referred to as "normal biopsy- or autopsy-derived tau" derived from "normal individuals", "non-AD patients" and "non-demented control individuals" in the remaining part of the present invention).

Presently known tau monoclonal antibodies recognize phosphorylation-dependent or phosphorylation-independent epitopes present on normal tau derived from freshly isolated brain biopsies or from autopsies derived from the brains of patients having died of diseases in which the occurence of NFT is not a pathological hallmark, confirming that these epitopes are not specific for the particular form or the particular subclass of phosphorylated tau as derived from the brains of patients having died from Alzheimer's disease.

Surprisingly, the present inventors have isolated and characterized a monoclonal antibody, AT100, which is recognizes specifically a subclass of phosphorylated tau and does not cross-react with biopsy- or autopsy-derived tau preparations of patients having died of diseases in which the occurrence of NFT is not a pathological hallmark. The present invention thus relates to any monoclonal antibody which has the reactivity characteristics in common with the monoclonal antibody AT100 as teached in the Examples section.

The monoclonal antibodies of the invention (AT100 or any other similar monoclonal antibody according to the present invention) may be selected from a range of monoclonal antibodies obtained by direct immunization with tau, extracted from human brain tissue derived from Alzheimer patients as illustrated in the examples section. More particularly, the monoclonal antibodies of the invention are characterized by the fact that they specifically bind to a phosphorylated epitope which is present in a particular subclass or form of phosphorylated tau and which is absent or non-detectable by the present methods (see examples section) in (i) fetal tau or in (ii) tau isolated from autopsy- or biopsy-derived brain material taken from individuals not suffering or having died from diseases in which NFT are a pathological hallmark (also referred to as non-AD patients, see above).

Further analysis of the epitopes recognized by these monoclonal antibodies showed that they are particularly directed at a phosphorylated epitope confined to a region of the tau molecule spanning positions 146 to 251 of the tau molecule as indicated in SEQ ID NO 1 (see below), more particularly to a region of the tau molecule spanning positions 198 to 251.

The monoclonal antibodies of the invention are further characterized by the fact that they recognize epitopes which are different from the epitope of the monoclonal antibody AT8 as defined in Goedert et al. (1993) and described in WO 93/08302 and the epitope of the monoclonal antibodies AT180 and AT270 as defined by Goedert et al. (1994) (described in International application PCT/EP 94/04146 filed on Dec. 14, 1994) and different from the epitopes recognized by the monoclonal antibodies BT2/Tau1 (Kosik et al., 1988), HT7 (Mercken et al., 1992a) or AT120 (International application published under WO 94/13795).

The monoclonal antibodies of the present invention are further characterized in that they specifically recognize a particular form or subclass of phosphorylated tau either on brain sections, on immunoblots of tau extracted from the brains of AD patients, in ELISA of tau extracted from the brains of AD patients or in body fluids such as CSF, either alone or in combination with other phosphorylated tau specific antibodies.

Said monoclonal antibody is being characterized by the the fact that it is capable of specifically detecting this epitope of phosphorylated tau which may be present in brain samples or body fluids such as cerebrospinal fluid (CSF).

The monoclonal antibodies of the invention are further characterized in that they specifically bind to and are capable to detect a particular phosphorylated epitope of the region of phosphorylated tau present in the brains of patients having died from AD (representing a particular subclass or form of phosphorylated tau) as specified in SEQ ID NO 1:

```
        146                 150                                    (SEQ ID NO 1)
NH2— Asp Gly Lys Thr Lys Ile Ala Thr Pro Arg 160                                                  170
    Gly Ala Ala Pro Pro Gly Gln Lys Gly Gln Ala Asn Ala Thr Arg

180
```

```
-continued

Ile Pro Ala Lys Thr Pro Pro Ala Pro Lys Thr Pro Pro Ser Ser
                190                                 200

Gly Glu Pro Pro Lys Ser Gly Asp Arg Ser Gly Tyr Ser Ser Pro
                                210

Giy Ser Pro Gly Thr Pro Gly Ser Arg Ser Arg Thr Pro Ser Leu
                220                                 230

Pro Thr Pro Pro Thr Arg Glu Pro Lys Lys Val Ala Val Val Arg
                                240

Thr Pro Pro Lys Ser Pro Ser Ser Ala Lys Ser Arg Leu Gln Thr
                250

Ala Pro Val Pro Met Pro COOH
```

The present invention relates more particularly to a monoclonal antibody as defined above, characterized by the fact it specifically forms an immunological complex:

either with a phosphorylated epitope located within the sequence as defined in SEQ ID NO 1, or with any other phosphorylated peptide capable of specifically forming an immunological complex with a monoclonal antibody, which itself is capable of forming a complex with a phosphorylated epitope located in the human tau protein region as shown in SEQ ID NO 1. The latter monoclonal antibody is characterized by the fact that it does not detect (i) fetal tau or (ii) biopsy- or autopsy-derived brain material from individuals not suffering or having died from diseases in which NFT is a pathological hallmark as seen in post-mortem samples collected at short (<24 h) post-mortem intervals or as seen in biopsy samples taken without post-surgical delay from patients suffering or having died from diseases in which NFT is not a pathological hallmark.

A preferred monoclonal antibody of the invention, AT100, is produced by the hybridoma deposited at ECACC (European Collection of Animal Cell Cultures, Vaccine Research and Production Laboratory, Public Health and Laboratory Service (PHLS), Centre for Applied Microbiology and Research, Porton Down, GB-Salisbury, Wiltshire SP4 OJG), on Apr. 21, 1994, under No 94042117.

The monoclonal antibodies of the invention are obtainable by a process involving obtention and isolation of hybridomas which secrete these monoclonal antibodies.

It is demonstrated in the examples section of the present invention, that the preferred monoclonal antibody of the invention allows the detection of a subclass of phosphorylated tau associated with AD whilst not detecting (ii) biopsy- or autopsy-derived tau from normal individuals or (ii) fetal tau.

A process for obtaining the hybridomas of the invention involves the steps of:

(a) starting from spleen cells of an animal, e.g. mouse or rat, previously immunized in vivo or in vitro with an antigen being chosen from the group of:
  phosphorylated tau present in brain extracts derived from the brains of patients having died of AD, or,
  a phosphorylated human tau peptide, or,
  immunoaffinity purified phosphorylated tauy extracted and purified from a human brain sample of a patient having died from Alzheimer's disease, recognized by the monoclonal antibodies of the invention;

(b) fusing said immunized cells with myeloma cells under hybridoma-forming conditions; and (c) selecting those hybridomas which secrete the monoclonal antibodies which are capable of specifically recognizing a phosphorylated epitope of tau present in a particular subclass or form of phosphorylated tau without recognizing (i) biopsy- or autopsy-derived tau from normal individuals or (ii) fetal tau from the brains of patients with diseases in which the occurence of NFT is not a pathological hallmark by means of Western blot analysis or ELISA.

The antigen of the invention is advantageously contained in brain and brain extracts, in the cerebrospinal fluid or the serum of a patient having Alzheimer's disease, Down syndrome, Pick's disease, subacute sclerosing panencephalitis (SSPE) or other neurological diseases in which NFT are a pathological hallmark; this antigen provokes an immunological reaction with the monoclonal antibody of the invention.

More particularly, the present invention relates also to monoclonal antibodies as defined above, obtainable by a process comprising at least the following steps:

(a) starting from the spleen cells of a mouse previously immunized with an antigen chosen from the following group:
  phosphorylated tau extracted and purified from a human brain sample of a patient having died from Alzheimer's disease (as disclosed in the examples section), or,
  a phosphorylated human tau peptide, or,
  immunoaffinity-purified phosphorylated tau extracted and purified from a human brain sample of a patient having died from Alzheimer's disease capable of reacting with the monoclonal antibodies of the invention, (b) fusing said immunized cells with myeloma cells under hybridoma-forming conditions, (c) selecting those hybridomas which secrete monoclonal antibodies which specifically recognize (a particular subclass or form of) phosphorylated tau without recognizing an epitope of (i) fetal tau or (ii) biopsy- or autopsy-derived tau material from the brains of normal individuals (as defined above) or patients having died or suffering from diseases in which NFT is not a pathological hallmark as determined by means of Western blot analysis or ELISA, (d) culturing the selected hybridomas as indicated above in an appropriate culture medium; and, (e) recovering the monoclonal antibodies secreted by said selected hybridoma; or alternatively, (f) implanting the selected hybridoma into the peritoneum of a mouse and, when ascites has been produced in the animal;

(g) recovering the monoclonal antibodies then formed from said ascites.

A process for producing the monoclonal antibodies of the invention involves at least the steps of:

(a) culturing the selected hybridomas as indicated above in an appropriate culture medium; and, (b) recovering the monoclonal antibodies secreted by said selected hybridoma; or alternatively, (c) implanting the selected hybridoma into the peritoneum of a mouse and, when ascites has been produced in the animal;

(d) recovering the monoclonal antibodies then formed from said ascites.

The monoclonal antibodies of the invention can be prepared by conventional in vitro techniques such as the culturing of immobilized cells using e.g. hollow fibers or microcapsules or such as the culturing of cells in homogeneous suspension using e.g. airlift reactors or stirred bioreactors.

The invention also relates to a peptide capable of forming an immunological complex with the monoclonal antibodies of the invention, with said peptide being in the phosphorylated form, and with the sequence of said peptide comprising, or consisting of phosphorylated parts or derivatives of the sequence as shown in SEQ ID NO 1, or, with the sequence of said peptide comprising, or consisting of the sequence of any phosphorylated peptide being capable of specifically forming an immunological complex with the monoclonal antibodies according to the invention.

Said phosphorylated peptides are preferably from 6 to 100 amino acids long. The peptides according to this embodiment of the invention can be prepared by classical chemical synthesis. The synthesis may be carried out in homogenous solution or in solid phase according to any of the techniques well known in the art.

Phosphorylated peptides are prepared according to any technique known in the art, (f.i. de Bont et al., 1990a; de Bont et al., 1990b; Perich, 1991; Otvos et al., 1989)

According to yet another embodiment, the present invention relates to a phosphorylated peptide as defined above, which is capable of generating a monoclonal antibody according to the present invention upon immunization.

The peptides used for immunization are preferentially in the form in which they are joined to a biotin molecule or any other carrier molecule in order to achieve a good immunogenic response. Such carrier molecules are well known in the art and are coupled to the peptide via linker groups, which are also comprised in the art.

The invention also relates to a process for in vitro the detection or diagnosis in vitro of a brain/neurological disease involving a particular form or subclass of phosphorylated tau, such as Alzheimer's disease, which comprises at least the following steps:

contacting a monoclonal antibody of the invention with a preparation of NFT, PHF or a detergent-extracted brain homogenate isolated from a patient having had Alzheimer's disease or any other disease involving phosphorylated tau protein under conditions suitable for producing an antigen-antibody complex;

detecting the immunological binding of said antibody to said brain homogenate, and possibly separating said complex and possibly recovering the antigen sought in a purified form.

Recovering the antigen sought may be done by first washing the immobilized antibody-antigen complex then formed;

treating this complex with a solution (e.g. 3 M potassium thiocyanate, 2.5 M magnesium chloride, 0.2 M citrate-citric acid, pH 3.5 or 0.1 M acetic acid) capable of producing the dissociation of the antigen-antibody complex; and;

recovering the antigen in a purified form.

The invention relates also to a process for the detection or diagnosis in vitro of brain/neurological disease involving a particular form or subclass of phosphorylated tau protein, such as in Alzheimer's disease, which includes:

bringing a sample of CSF, more preferably unconcentrated CSF, or a sample of serum, or proteins or polypeptides as a result of an extraction procedure starting from brain tissues, cerebrospinal fluid or serum known to those skilled in the art (Ibqal et al., 1984; Greenberg & Davies, 1990) from a patient suspected of suffering from brain disease involving NFT, more particularly Alzheimer's disease, into contact under in vitro conditions with a monoclonal antibody of the invention, with said conditions being suitable for producing an antigen-antibody complex; and, detecting the immunological binding of said antibody to said sample of brain extract, cerebrospinal fluid or serum.

Advantageously, the monoclonal antibodies of the invention are in an immobilized state on a suitable support such as a resin. Alternatively, the present process may be put into practice by using any other immunoassay format known to the person skilled in the art.

The process for the detection of the antigen can then be carried out by bringing together said antigen-antibody complex formed by the antigen and the antibodies of the invention with:

a) a second antibody which can be a monoclonal antibody recognizing an epitope of tau protein or phosphorylated tau protein, or of any tau peptide carrying an epitope, with said epitope being different from the one of the invention, or which can be a polyclonal antibody recognizing tau protein or phosphorylated tau or a polyclonal antibody recognizing a tau peptide, with said polyclonal antibody being capable of forming an immunological complex with epitopes which are different from the epitope of the invention, with said polyclonal antibody being preferably purified by immunoaffinity chromatography using immobilized tau protein or phosphorylated tau protein;

(b) a marker either for specific tagging or coupling with said second antibody, with said marker being any possible marker known to the person skilled in the art;

(c) appropriate buffer solutions for carrying out the immunological reaction between the monoclonal antibody of the invention and a test sample on the one hand, and the bound second antibody and the marker on the other hand, and, (d) possibly also a peptide carrying a phosphorylated epitope of tau comprised in the region spanning SEQ ID NO 1 for standard purposes, or for competition purposes with respect to the antigen which is sought.

Advantageously, the second antibody itself carries a marker or a group for direct or indirect coupling with a marker.

The monoclonal antibodies of the invention enable the diagnosis of Alzheimer's disease (AD) and of any disease involving the formation of NFT on the basis of CSF, brain extract, serum samples or brain sections (i.e. to detect particular subclasses of phosphorylated tau).

The results obtained with the monoclonal antibodies of the invention indicate that the epitope recognized by the monoclonal antibodies of the invention is specifically found in phosphorylated tau derived from the brains of patients having died or suffering from Alzheimer's disease, but may occur also in other neurological diseases where the presence of NFT constitutes a pathological hallmark and are not found in preparations of tau derived from biopsy or autopsy brain material of normal individuals (as defined above) or patients having a disease in which NFT is not a pathological hallmark.

According to another embodiment, the present invention relates to a kit for the diagnosis in vitro of one of the following diseases: Alzheimer's disease, Down's syndrome, Pick's disease and other neurological disorders in which phosphorylated tau protein, NFT or paired helical filaments are implicated, characterized in that the kit comprises:

- at least a microplate for deposition thereon of at least a monoclonal antibody of the invention;
- a second antibody
    - which can be a monoclonal antibody recognizing an epitope of tau protein or phosphorylated tau protein, or of any phosphorylated tau peptide carrying an epitope, with said epitope being different from the one of the invention, or
    - which can be a polyclonal antibody recognizing tau protein or phosphorylated tau or a polyclonal antibody recognizing a peptide carrying an epitope of tau, with said polyclonal antibody being capable of forming an immunological complex with epitopes which are different from the epitope of the invention, with said polyclonal antibody being preferably purified by immunoaffinity chromatography using immobilized tau protein;
- a marker either for specific tagging or coupling with said second antibody;
- appropriate buffer solutions for carrying out the immunological reaction between the monoclonal antibody of the invention and a test sample on the one hand, and the bound second antibody and the marker on the other hand,
- possibly also a peptide carrying a phosphorylated epitope of tau comprised in the region spanning SEQ ID NO 1 for standard purposes, or for competition purposes with respect to the antigen which is sought.

The present invention also relates to a kinase which upon acting on non-phosphorylated tau is capable to specifically introduce a phosphorylation in the region as specified in SEQ ID NO 1, thereby giving rise to the epitope recognized by the monoclonal antibody of the invention.

The invention also relates to a phosphorylase which is capable to react specifically with the epitope recognized by a monoclonal antibody according to the present invention comprised in SEQ ID NO 1, thereby destroying the epitope in such a way that an immunological reaction can no longer take place between said peptide and the monoclonal antibody of the invention.

The present invention further relates to a method for screening for compounds which interfere with the activity of the above-mentioned kinase comprising the steps of:

- bringing into contact non-phosphorylated tau or a non-phosphorylated peptide of which the sequence comprises or consists of the sequence specified in SEQ ID NO 1,
- with a kinase as defined above capable of phosphorylating tau protein or a polypeptide which contains at least the sequence as specified in SEQ ID NO 1, or derivatives thereof, thereby producing the epitope recognized by the monoclonal antibody of the invention,
- and any compound which is capable to interfere with the process of phosphorylation of said epitope by said kinase,
- and detecting the amount of phosphorylation using the monoclonal antibody of the present invention as defined above.

The present invention further relates to a method for screening for compounds which interfere with the activity of the above-mentioned phosphorylase comprising the steps of:

- bringing into contact phosphorylated tau or a phosphorylated peptide of which the sequence comprises or consists of the phosphorylated sequence specified in SEQ ID NO 1 or phosphorylated derivatives thereof, and which is recognized by the monoclonal antibodies of the invention,
- with a phosphorylase capable to remove phosphate from said phosphorylated tau or said phosphorylated peptide,
- and detecting the amount of dephosphorylation by means of e.g. and ELISA assay comprising the monoclonal antibody of the invention as defined above.

DEFINITIONS

The expression "phosphorylated tau" as used in the present invention refers to PHF-tau (also known as "abnormally phosphorylated tau") and biopsy-derived normal tau. The latter has been shown by the present inventors to be also phosphorylated, in contradiction to what was previously thought to be the case.

The expression "specifically bind to and are capable to detect a phosphorylated epitope present in a particular form or subclass of phosphorylated tau" corresponds to the fact that the monoclonal antibodies of the invention detect a particular form or subclass of phosphorylated tau which is predominantly present in PHF derived from brains from AD patients and which is absent, or not detectable by the present methods, in the brains of human foetuses, of non-demented control patients as seen in postmortem samples collected at short (<24 h) post-mortem intervals or in biopsy samples taken without post-surgical delay (<15 min.). Non-demented control patients or normal individuals are further defined as patients not suffering from diseases in which NFT are a pathological hallmark and which are defined as normal according to the NINCDS-ADRA (McKahn et al., 1984) or the DSM (Diagnostic and Statistical Manual of Mental Disorders—III, American Physchiatric Association, Washington DC, 1987).

The expression "an epitope which is absent or non-detectable by the present methods" refers to the methods as described in the examples section, such as ELISA, competition ELISA, RIA, and other well known methods to the person skilled in the art.

The expression "form an immunologically complex with" is to be interpretated such that the monoclonal antibody of the invention binds to the above-said antigen under conditions as mentioned in one of the following techniques:

Light immunomicroscopy

Post-mortem tissue was obtained from histologically confirmed Alzheimer patients. Immediately after excision, the brain biopsy was immersed in ice-cold phosphate buffered-saline and processed for: (1) the preparation of enriched tau fractions without post-surgical delay; (2) for immunocytochemistry following fixation in isotonic 70% ethanol. Following fixation, the tissue samples were infiltrated and embedded in paraffin (Trojanowski et al., 1989), and 6 $\mu$m thick sections were cut from paraffin blocks of the biopsy and autopsy brain samples. Immunohistochemistry using the peroxidase anti-peroxidase method, and the microscopic assessment of the tissue to identify evidence of AD or other types pathological abnormalities were performed as described previously (Bramblett et al., 1992; Lee et al., 1993; Trojanowski et al., 1989).

Other brain tissue samples, of e.g. Alzheimer patients obtained at surgery or autopsy, were fixed by immersion in 4% formalin or Bouin's fixative and embedded in paraffin for sectioning. The monoclonal antibodies of the invention are applied in conjunction with a technique to visualize the formed immune complexes such as the avidin-biotinylated peroxidase complex technique (Hsu et al., 1981) using 3,3'-diaminobenzidine tetrahydrochloride for development of color. Sections were counterstained with Harris haematoxylin stain.

Immunoblotting procedures

For immunoblotting, fractions enriched in phosphorylated tau are prepared as described (Greenberg and Davies, 1990). Typically, biopsy or postmortem tissue, consisting mostly of gray matter from the frontal and temporal cortex, was homogenized with 10 volumes of cold buffer H (10 mM Tris/1 mM EGTA/0.8 M NaCl/10% sucrose, pH 7.4) in a Teflon/glass Potter S (Braun, Germany) homogenizer. After centrifugation of the homogenate in a 60 Ti MSE rotor at 27,000×g for 20 min at 4° C., the pellet was removed and the supernatant was adjusted to 1% (wt/vol) N-laurosylsarcosine and 1% (vol/vol) 2-mercaptoethanol and incubated while rotating on a mixer for 2.5 hours at 37° C. The supernatant mixture was centrifuged at 108,000×g for 35 min at 20° C. The PHF-tau containing pellet was gently washed with PBS and finally suspended in 1 ml of the same buffer.

Normal tau was isolated from brain samples derived from non-demented persons or from patients suffering from diseases in which the presence of NFT is not a pathological hallmark. These samples were homogenized in ice cold reassembly (RA) buffer (0.1 M MAS, 0.5 mM MgSO$_4$, 1 mM EGTA, 2 mM dithiothreitol [pH 6.8]) containing 0.75 M NaCl, and a cocktail of protease and phosphatase inhibitors (2 mM phenylmethysulfonyl fluoride, 20 mM NaF, 0.5 mM sodium orthovanadate, and TPCK, TLCK, leupeptin, pepstatin, soy bean trypsin inhibitor and apotinin, each at 1 $\mu$g/ml. After centrifugation at 50,000×g for 30 min at 4° C., the supernatants were boiled for 10 min, and recentrifuged at 50,000×g for 30 min.

SDS-polyacrylamide electrophoresis is performed under reducing conditions on 12% gels (Laemmli, 1970). After electrophoresis, the proteins are either fixed and stained with Coomassie brilliant blue, or transferred (Towbin et al., 1979) to nitrocellulose sheets (Hybond-C, Amersham) or Immobilon filters (Millipore).

After transfer, the filters are presoaked in PBS containing 0.05% (v/v) Tween 20 (Tween-PBS) and then incubated for 1 h in Tween-PBS containing 5% (w/v) skimmed dried milk and 10% (v/v) newborn calf serum (blocking buffer). Next, the filters are treated overnight at 4° C. with the monoclonal antibody of the invention appropriately diluted in blocking buffer.

The filters are then washed three times in Tween-PBS and treated for 1.5 h at room temperature with horseradish peroxidase-labeled rabbit anti-mouse IgG (Dakopatts, Denmark) diluted 1/3000 in blocking buffer. After three washes in Tween-PBS, streptavidine-biotinylated horseradish peroxidase complex (Amersham), diluted 1/250 in blocking buffer, is applied for 1.5 h at room temperature. Thereafter, the filters are washed three times in Tween-PBS and once in PBS. The filters are then incubated in PBS containing 0.05% (w/v) diaminobenzidine and 0.03% (v/v) hydrogen peroxide until background staining develops.

It should be clear that the formation of an immunological complex between the monoclonal antibodies and the antigen is not limited to the precise conditions described above, but that all techniques that respect the immunochemical properties of the antibody and antigen binding will produce similar formation of an immunological complex.

The terms "recognizing", "detecting", "forming an immunological complex with" or "reacting" as used in the present invention particularly relate to specifically recognizing, detecting or reacting.

The expression "phosphorylated human tau peptide" refers to a peptide comprising in its amino acid sequence a phosphorylated sequence of human tau protein extracted from the brains of a patient having died from AD and with said sequence being characterized by the fact that it can specifically form an immunological complex with the antibodies of the invention.

The term derivatives as used in the present invention designates any known protein or peptide derivative known in the art which mimics the immunological reactivity of the protein or peptide it is derived from.

EXAMPLES

Example 1

Preparation of the Monoclonal Antibodies AT100 Using Tau Isolated from an AD Patient as Antigen 1. Preparation of the Antigen for Immunization Tau from an AD patient (or PHF-tau) was partially purified by a modification of the method of Greenberg and Davies (1990). Postmortem tissue, consisting mostly of gray matter from the frontal and temporal cortex, was obtained from histologically confirmed Alzheimer patients. This Alzheimer gray matter brain sample (5–10 g) was homogenized with 10 volumes of cold buffer H (10 mM Tris/1 mM EGTA/0.8 M NaCl/10% sucrose, pH 7.4) in a Teflon/glass Potter S (Braun, Germany) homogenizer. After centrifugation of the homogenate in a 60 Ti MSE rotor at 27,000×g for 20 min at 4° C., the pellet was removed and the supernatant was adjusted to 1% (wt/vol) N-laurosylsarcosine and 1% (vol/vol) 2-mercaptoethanol and incubated while rotating on a mixer (Swelab, Sweden) for 2.5 hours at 37° C. The supernatant mixture was centrifuged at 108,000×g for 35 min at 20° C. The PHF-tau containing pellet was gently washed with PBS and finally suspended in 1 ml of the same buffer.

The antigen preparation was evaluated by a 10% sodium dodecyl sulfate-polyacrylamide gel electrophoresis, followed by Western blotting using polyclonal rabbit anti-human normal tau antiserum (Mercken et al., 1992a).

2. Immunization Protocol and Fusion Procedure

Balb/c mice were primed subcutaneously with 100 $\mu$g of a tau preparation derived from the brain of a patient having died from AD in complete Freund's adjuvant and boosted intraperitoneally 3 times thereafter at 3-week intervals with 100 μg of the same antigen in incomplete Freund's adjuvant. On days 3 and 2 before the fusion, mice were boosted with 100 μg PHF-tau in saline.

Mouse spleen cells were fused with SP2/0 myeloma cells, using a modified procedure of Köhler and Milstein (1975), with PEG 4000.

The cells of the fusion experiment were suspended at a density of $4.5 \times 10^4$ spleen cells/well on 96-well plates pre-seeded with mouse peritoneal macrophage cells as a feeder layer. These wells were screened after 12 days of continuous growth for anti-PHF-tau antibody production by means of a sandwich ELISA as detailed below.

Hybridoma growth was performed in Dulbecco's modified Eagle's medium (DMEM) supplemented with 20% fetal calf serum, sodium pyruvate (1 mM), L-glutamine (2 mM), penicillin (100 U/ml), streptomycin (100 mg/ml), and non-essential amino acids. All products were purchased from Gibco, (Paisley, U.K.). Cells were incubated in a humidified $CO_2$-air incubator.

3. Sandwich ELISA for Screening for Antibodies which React with Phosohorylated tau of a Patient Having Died from AD The screening ELISA used for the detection of monoclonal antibodies directed to phosphorylated epitopes of tau was a sandwich ELISA system with affinity-purified polyclonal rabbit anti-human tau antibodies (Mercken et al., 1992a) in the coating phase. To this end, purified human normal tau, prepared as described in Mercken et al. (1992a) was used for the preparation of an immuno-affinity column using covalent immobilization on cyanogen bromide-activated Sepharose (Pharmacia, LKB Sweden). The affinity-bound anti-tau fraction was eluted from this column with a 0.1 M citric acid buffered solution at pH 2.5. After neutralization, the anti-tau-containing fractions were pooled and coated overnight (1 μg/ml) at 4° C. on high-binding microtiter plates (Nunc, Gibco, Paisley, UK) in coating buffer (10 mM Tris, 10 mM NaCl, 10 mM $NaN_3$, pH 8.5). After overcoating for 30 min with 125 μl 10%-saturated casein in PBS to reduce non-specific binding, the plates were incubated with 100 μl of an appropriately diluted phosphorylated tau isolated from a patient having died from AD preparation and incubated for 60 min at 37° C. The plates were washed 3 times with PBS-0.05% Tween 20 (v/v); 100 μl hybridoma supernatant was added and incubation was continued for 1 h at 37° C. After washing, the bound monoclonal antibodies were detected with peroxidase-conjugated rabbit anti-mouse serum (Dakopatts, Glostrup, Denmark). All reagents were diluted in PBS with 10% casein. After final washing, 100 μl 0.42 mM 3,5,3',5'-tetramethylbenzidine, 0.003% $H_2O_2$ v/v in 100 mM citric acid, 100 mM disodium hydrogen phosphate, pH 4.3, was added as peroxidase substrate. The reaction was stopped with 50 μl of a 2 M $H_2SO_4$ solution. Absorbance was read in a Titertek Multiscan (Flow Laboratories, Eflab, Oy, Finland) at 450 nm.

From such a fusion experiment, using the screening procedure as described in section 3 above, 28 positive cultures (i.e. anti-PHF-tau antibodies-secreting cultures) were retrieved out of a total of 1440 cultures. These positive cultures were arbitrarily designated AT1 to AT28 (some of these hybridoma cultures, i.e. AT1 to AT14 are described by Mercken et al., 1992b). As in this initial screening round positive cultures were mostly found to be composed of mixed clones as seen by visual inspection of the wells (usually between 1 and 4 clones per well), all hybridoma cultures were further subcloned by limiting dilution, a technique well known to those skilled in the art, finally resulting in pure hybridoma clones secreting antibodies with a homogeneous idiotype. Some of these pure hybridoma clones were further tested with respect to their reactivity patterns on normal and phosphorylated tau in ELISA as described in Example II and by Western blotting and to the location of their epitopes. From these results AT100 was selected.

The Western blotting procedure was carried out as follows:

Purified normal human tau and phosphorylated tau derived from the brain of patients having died from Alzheimers disease were applied to 10% SDS-polyacrylamide gels and run under denaturing conditions according to Laemmli (1970).

After SDS-PAGE, the transfer to nitrocellulose (Hybond-C, Amersham, Brussels, Belgium) was carried out in 10 mM NaHCO3, 3 mM Na2CO3, pH 9.9 for 120 min at 55 V with cooling. After blotting, the nitrocellulose was equilibrated to phosphate buffered saline (PBS), and protein binding sites were blocked with blot buffer (PBS supplemented with 5% w/v skimmed dried milk and 10% v/v newborn calf serum). Blotted proteins were incubated overnight at 4° C. with the antibody of the respective hybridoma. After three washings with PBS-0.05% Tween 20 (v/v), horseradish peroxidase-labeled rabbit anti-mouse immunoglobulins (Dakopatts, Glostrup, Denmark) were used at a dilution of ⅓₀₀₀ and were incubated for 90 min at room temperature. All antisera were diluted in blot buffer. The blots were then washed three times in PBS/Tween and developed with substrate solution (PBS, 0.05% w/v 3,3'-diaminobenzidine, 0.03% v/v H202) after which the reaction was stopped in H20.

As a result of these analyses, 8 hybridomas out of 28 (including AT3, AT8 (Mercken et al.), AT100, AT180 and AT270 (European Patent Application N° 94303133.7) were found to recognise phosphorylated tau isolated from a patient having died from AD (PHF-tau).

Finally the monoclonal antibodies secreted by the hybridomas AT8, AT100, AT180 and AT270 were screened with extracts of brain samples obtained from fetal brain, adult brain and brain biopsies of non-demented patients or post-mortem tissue of patients having died from AD and their reactivity patterns were compared with those obtained with other well-characterized monoclonal antibodies such as T41/46, T1, AT8, T3P, PHF1, AT180 and AT270 (see above). Western blotting analysis indicated that AT100 secreted monoclonal antibodies were clearly distinct from well-known other monoclonal antibodies in that the monoclonal antibodies of the invention reacted only with phosphorylated tau as extracted from AD brain and not with tau and phosphorylated tau which can be found in the brain of human foetuses, of adults or of biopsies derived from patients not suffering from a disease in which the presence of NFT is a pathological hallmark.

4. Determination of the Antibody Class and Subclass

The antibody class and subclass was determined by Inno-LIA (Innogenetics, Ghent, Belgium). The antibodies secreted by AT100 appeared to be of the IgG1, kappa subtypes.

Example 2

Characterization of Antibodies which React with Phosphorylated Tau Extracted from a Patient Having Died from AD and their Epitopes 1. Discrimination of Phosphorylated tau from AD Patients from Normal tau in ELISA The preparation of affinity purified normal tau is described in Mercken et al. (1992b) and for phosphorylated-tau isolated from the brain of a patient having died from AD is essentially as described in Greenberg and Davies (1990); Mercken et al. (1992a). Purity of normal tau and phosphorylated-tau standards was determined by SDS-PAGE. The samples were also analyzed on 420 A/H amino acid analyzer (Applied Biosystems B. V., Maarssen, The Netherlands) according to the manufacturer's instructions. Both normal and phosphorylated tau showed the expected amino acid compositions. The exact protein concentration of both affinity purified normal and phosphorylated tau was determined using an internal standard peptide.

The monoclonal antibodies derived from the hybridomas AT100 and purified from serum-free conditioned medium by Protein G column chromatography, were coated overnight at 4° C. on high-binding microtiter plates (Nunc, Gibco, Paisley, UK) in coating buffer at 3 μg/ml (10 mM Tris, 10 mM NaCl, 10 mM NaN$_3$, pH 8.5). After overcoating for 30 min with 150 μl 10%-saturated casein in PBS to reduce non-specific binding, the plates were incubated with 100 μl of an appropriately diluted tau preparation or of a phosphorylated tau preparation derived from the brain of a patient having died from D as standards and incubated for 60 min at 37° C. The plates were washed 5 times with PBS-0.05% Tween 20 (v/v) and 100 μl of two biotinylated antibodies (AT120 and HT7, Vandermeeren et al., 1993; Mercken, Ph. D. thesis) at a final concentration of 0.2 μg/ml was added and incubated for 1 hr at room temperature. After washing, horse-radish peroxidase conjugated streptavidine (Jackson, Innogenetics, Belgium) at a dilution of 1/10000 was added for 30 min at room temperature. Following a final washing with PBS/Tween 20, 100 μl of 0.42 mM 3,5,3',5'-tetramethylbenzidine, 0.003% (vol/vol) H$_2$O$_2$ in 100 mM citric acid, 100 mM Na$_2$HPO$_4$, pH 4.3 were added as peroxidase substrate for 30 min at room temperature. The reaction was stopped with 50 μl of a 2 M H$_2$SO$_4$ solution. Absorbance was read in a Titertek Multiscan (Flow Laboratories, Eflab Oy, Finland) at 450 nm.

Under conditions in which 500 ng antigen was present, AT100 did not react with tau derived from patients having died of diseases in which NFT are not a pathological hallmark.

2. Mapping of the AT100 Epitope to the Proline-rich Region

100 μg purified AD specific tau proteins (Greenberg and Davies, 1990 or Bramblett et al., 1993) was digested with Endoprotease AspN (Boehringer) according to the manufacturer's instructions. The digested proteins were loaded on an SDS-tricine acrylamide gel (16.5%, Schägger et al., 1987). Gels were blotted on PVDF membranes, blocked and AT100 reactive bands were revealed. Two bands were immunoreactive and N-terminally sequenced. Results of the sequence analysis is shown in Table 1. Based on these results, the epitope of AT100 can be condluded to lie in the region spanning positions 146 to 251, more particularly in the region spanning positions 198 to 251, of the tau protein.

Example 3

Reactivity of Monoclonal Antibodies each Recognising a Different Phosphoyrylated tau Epitope on Extracts of Human tau Derived from AD Brain, Fetal Brain or Biopsies Obtained from Patient Suffering of Diseases for which the Presence of NFT is not a Pathological Hallmark Brain extracts were prepared from human biopsy samples, obtained from lateral temporal lobe, from autopsy-derived fetal brain, from autopsy-derived human adult tau (11 hr postmortem time) or from autopsy-derived human brain from patients having died of AD as described above. Samples of these extracts were loaded onto 10% SDS-PAGE gels and after electrophoresis were blotted onto nitrocellulose sheets (Wester, blotting). The sheets were probed with each of the following antibodies

| Antibody code | Recognition site/epitope |
|---|---|
| AT270 | phosphothreonine (S181) |
| AT8 | phosphoserine (S202, T205) |
| AT180 | phosphothreonine (S231) |
| T3P | phosphoserine (S396, S404) | and counterstained with $^{125}$I-labeled goat anti-mouse IgG. Under these circumstances, a clear signal is obtained with extracts from autopsy-derived human brain from patients having died from AD, a statistically non-significant signal is present for biopsy-derived tau, while fetal-derived and adult-derived tau are also negative or non-significant. In contrast, other monoclonal antibodies are positive for fetal-derived and/or biopsy-derived adult tau, as well as for phosphorylated tau derived from Alzheimer disease brains.

TABLE 1

| Band | MW | AT100 | Sequence | Positions | |
|---|---|---|---|---|---|
| 1 | 2 kD | − | NNNNGTKIG<br>G<br>L | 259–282 | (SEQ ID NO:2) |
| 2 | 2 kD | − | | | |
| 3 | 3 kD | − | | | |
| 4 | 4 kD | − | DNIRRIP<br>KNVHAA<br>GAVH<br>ARKG<br>P | 146–197 | (SEQ ID NO:3) |
| 5 | 14 kD | + | DGTRVIAGVSXXKGG<br>SPE AST<br>K    L | 146–251 | (SEQ ID NO:4) |
| 6 | 15 kD | − | | | |
| 7 | 16 kD | − | | | |
| 8 | 17 kD | − | | | |
| 9 | 18 kD | + | DGPEQXD | 54–251 | (SEQ ID NO:5) |

TABLE 1-continued

| Band MW | AT100 Sequence | Positions |
|---|---|---|
| | ERA | |
| | L | |

REFERENCES

Andreadis A, Brown W, Kosik K (1992) Structure and novel exons of the human tau gene. Biochem 31:10626–10633.

Binder L, Frankfurter A, Rebhun L (1985) The distribution of tau in the mammalian central nervous system. J. Cell. Biol. 101(4):1371–8

Bramblett G, Trojanowski J, Lee V (1992) Regions with abundant neurofibrillary pathology in human brain exhibit a selective reduction in levels of binding-competent tau and accumulation of abnormal tau isoforms (A68 proteins). Lab Invest 66:212–222.

Bramblett G, Goedert M, Jakes R, Merrick S, Trojanowski J, Lee V (1993) The abnoramal phosphorylation of tau at Ser396 in Alzheimer's disease recapitulates phosphorylation during development and contributes to reduced microtubule binding. Neuron 10:1089–1099.

Brion J, Passareiro J, Nunez J and Flament-Durand J (1985) Mise en evidence immunologique de la proteine tau au niveau des lesions de degenerescence neurofibrillaire de la maladie d'Alzheimer. Arch Biol 95:229–235.

Biernat J, Mandelkow M, Schoter C, Lichtenberg-Kraag B, Steiner B, Berling B, Meyer H, Mercken M, Vandermeeren M, Mandelkow E, The switch of tau protein to an Alzheimer-like state includes the phosphorylation of two serine-proline motifs upstream of the microtubule binding region. EMBO J, 1992, 11:1593–1597.

Bobrow M, Harris T, Shaughnessy K, Litt G (1989) Catalyzed reporter deposition, a novel method of signal amplification. Application to immunoassays. J Immunol Meth 125:279–285.

Butner K, Kirschner (1991) Tau protein binds to microtubules through a flexible array of distributed weak sites. J Cell Biol 115:717–730.

de Bont H, van Boom J, Liskamp R (1990a) Automatic synthesis of phosphopeptides by phosphorylation on the solid phase. Tetrahedron Letters 31:2497–2500.

de Bont H, van Boom J, Liskamp R (1990b) N,N-diiopropyl-bis(4-chlorobenzyl)phosphoramidite: A versatile phosphitylating agent for the phosphorylation of hydroxy amino acids and preparation of protected phosphopeptides. Recueil des Travaux Chimiques des Pays-bas 109:27–28.

Delacourte A, Flament S, Dibe E, Hublau P, Sablonniere B, Hemon B, Sherrer V, Defossez A (1990) Pathological proteins Tau64 and 69 are specifically expressed in the somatodendritic domain of the degenerating cortical neurons during Alzheimer's disease. Acta Neuropathol 80:111–117.

Delacourte A, Défossez A (1986) Alzheimer's disease: Tau proteins, the promoting factors of microtubule assembly, are major components of paired helical filaments. J. Neurol. Sci. 76:1 73–180.

Drewes G, Lichtenberg-Kraag B, Doring F, Mandelkow E-M, Biernat J, Goris J, Doree M, Mandelkow E (1992) Mitogen activated protein (MAP) kinase transforms tau protein into an Alzheimer-like state. EMBO J 11:2131–2138.

Flament S, Delacourte A, Hemon B, Defossez A (1989) Characterization of two pathological Tau protein variants in Alzheimer brain cortices. J Neurol Sci 92:133–141.

Flament S, Delacourte A (1990) Tau Marker? Nature 346:6279.

Flament S, Delacourte A, Mann D (1990) Phosphorylation of tau proteins: a major event during the process of neurofibrillary degeneration. A comparitive study between Alzheimer's disease and Down's syndrome. Brain Res 516:15–19.

Ghanbari H, Kozuk T, Miller B, Riesing S (1990) A sandwich enzyme immunoassay for detecting and measuring Alzheimer's disease-associated proteins in human brain tissue. J Clin Laboratory Anal 4:189–192.

Goedert M, Wishik C, Crowther R, Walker J, Klug A (1988) Cloning and sequencing of the cDNA encoding a core protein of the paired helical filament of Alzheimer disease: identification as the microtubuli-associated protein tau. Proc Natl Acad Sci (USA) 85:4051.

Goedert M, Spillantini M, Jakes R, Rutherford D, Crowther R (1989) Multiple isoforms of human microtubule-associated protein tau: sequences and localization in neurofibrillary tangles of Alzheimer's disease. Neuron 3:519–526.4055.

Goedert M, Jakes R (1990) Expression of seperate isoforms of human tau protein: correlation with the tau protein in brain and effects on tubulin polymerization. EMBO J 9:4225–4230.

Goedert M, Spillantini M, Jakes R (1991) Localization of the Alz-50 epitope in recombinant human microtubule-associated protein tau. Neurosci Lett. 126:149–154.

Goedert M, Cohen E, Jakes R, Cohen P (1992) p42 Map kinase phosphorylation sites in microtubule-associated protein tau one dephosphorylated by protein phosphatase 2A1: implications for Alzheimer's disease. FEBS Lett. 312:95–99.

Goedert M, Jakes R, Crowther R, Six J, Lübke U, Vandermeeren M, Cras P, Trojanowski J Q, Lee V (1993) The abnormal phosphorylation of tau protein at serine 202 in Alzheimer's disease recpitulates phosphorylation during development. Proc Natl Acad Sci (USA) 90:5066–5070.

Goedert M, Jakes R, Crowther R (1994) Epitope mapping of monoclonal antibodies to the paired helical filaments of Alzheimer's disease: identification of phosphorylation sites in tau protein. Biochem J (in press).

Greenberg S, Davies P (1990) A preparation of Alzheimer paired helical filaments that displays distinct tau proteins by polyacrylamide gel electrophoresis. Proc Natl Acad Sci USA 87:5827–5831.

Greenberg S, Davies P, Schein J, Binder L (1992) Hydrofluoric acid-treated tauPHF proteins display the same biochemical properties as normal tau. J Biol Chem 267:564–569.

Grundke-Iqbal I, Iqbal K, Tung Y, Quinlan M, Wisniewski H Binder L (1986) Abnormal phosphorylation of the microtubule-associated protein (tau) in Alzheimer's cytoskeletal pathology. Proc Natl Acad Sci (USA) 83:4913–4917.

Grundke-Iqbal I, Iqbal K, Quinlan M, Tung Y, Zaidi M, Wisniewski H (1986) Microtubule-associated protein tau. J Biol Chem 261:6084–6089.

Harrington C, Mukaetova E, Hills R, Edwards P, Montejo de Garcini E, Novak M, Wischik C (1991) Measurement of distinct immunochemical presentations of tau protein in Alzheimer's disease. Proc Natl Acad Sci (USA) 88:5842–5846.

Hasegawa M, Morishima-Kawashima M, Takio K, Suzuki M, Titani K, Ihara Y (1992) Protein sequence and mass spectrometric analyses of tau in Alzheimer's disease brain. J Biol Chem 267:17047–17054.

Himmler A (1989) Structure of the bovine tau gene: alternatively spliced transcripts. Mol. Cell Biol. 9(4):1389–96.

Hsu S, Raine L, Fanger H (1981) Use of avidin-biotin-peroxidase complex (ABC) in immunoperoxidase techniques: a comparison between ABC and unlabeled antibody (PAP) procedures. J Histochem Cytochem 29:577–580.

Iqbal K, Zaidi T, Thompson C, Merz P, Wisniewski H (1984) Alzheimer paired helical filaments: bulk isolation, solubility, and protein composition. Acta Neuropathol 62:167–177.

Iqbal K, Grundke-Iqbal I, Smith A, George L, Tung Y, Zaidi T (1989) Identification and localization of a Tau peptide to paired helical filaments of Alzheimer's disease. Proc Natl Acad Sci (USA) 86:5646–5650.

Ishiguro K, Takamatsu M, Tomizawa K, Omori A, Takahashi M, Arioka M, Uchida T, Imahori K (1992) Tau protein kinase I converts noraml tau protein into AA68-like component of paired helical filaments. J Biol Chem 267:10897–10901.

Kanai Y, Chen J, Hirokawa N (1992) Microtubule bundling by tau proteins in vivo: analysis of functional domains. EMBO J 11:3953–3961.

Köhler G, Milstein C (1975) Continuous cultures of fused cells secreting antibody of predefined specificity. Nature 256:495–497.

Kondo J, Honda T, Mori H, Hamada Y, Miura R, Ogawara M, Ihara Y (1988) The carboxyl third of tau is tightly bound to paired helical filaments. Neuron 1:82

Kosik K, Joachim C, Selkoe (1986) Microtubule-associated protein tau is a major antigenic component of paired helical filaments in Alzheimer's disease. Proc Natl Acad Sci (USA) 83:4044–4048.

Kosik K (1988) Epitopes that span the tau molecule are shared with paired helical filaments. Neuron. 1 (9):817–25.

Labbé J, Cavadore J and Dorée M (1991) M phase-specific cdc2 kinase: preparation from starfish oocytes and properties. Meth Enzymol 200:291–301.

Laemmli U (1970) Cleavage of structural proteins during the assembly of the head of bacteriophage T4. Nature 227:680–685.

Ledesma M, Correas I, Avila J, Diaz-Nido J (1992) Implication of brain cdc2 and MAP2 kinases in the phosphorylation of tau protein in Alzheimer's disease. FEBS Letters 308:218–224.

Lee V, Balin B, Otvos L, Trojanowski J (1991) A68: a major subunit of paired helical filaments and derivatized forms of normal tau. Science 251(4994):675–8.

Lewis S, Wang D, Cowan N (1988) Microtubule-associated protein MAP2 shares a microtubule binding motif with Tau protein. Science 242:936–939.

Mandelkow E-M, Drewes G, Biernat J, Gustke N, Van Lint J, Vandenheede J, Mandelkow E (1992) Glycogen-synthase kinase-3 and the Alzheimer's-like state of microtubule-associated protein tau. FEBS Letters 314:315–321.

Martin J, Gheuens J, Bruyland M, Cras P, Vandenberghe A, Masters C, Beyreuther K, Dom R, Ceuterick C, Lubke U, Van Heuverswijn H, De Winter G, Van Broeckhoven C (1991) Early_onset Alzheimer's disease in 2 large Belgian families. Neurology 41:62–68.

McKahn G, Drachman D, Folstein M, Katzman R, Price D, Stadlan E (1984) Clinical diagnosis of Alzheimer's disease: report of the NINCDS-ADRA work group under the auspices of department of health and human services task force on Alzheimer's disease. Neurology 34:939–944.

Mc Leod M, Stein M, and Beach D (1987) The product of the mei3+ gene, expressed under control of the mating-type locus, induces meiosis and sporulation in fision yeast. EMBO J 6:729–736.

Mercken M, Vandermeeren M, Lubke U, Six J, Boons J, Vanmechelen E, Van de Voorde A, Gheuens J (1992a) Affinity purification of human tau proteins and the construction of a sensitive sandwich enzyme-linked immunosorbent assay for human tau detection. J Neurochem 58:548–553.

Mercken M, Vandermeeren M, Lubke U, Six J, Boons J, Van de Voorde A, Martin J J, Gheuens J (1992b) Monoclonal antibodies with selective specificity for Alzheimer Tau are directed against phosphatase-sensitive epitopes. Acta Neuropathol 84:265–272.

Otvos L, Elekes I, Lee V (1989) Solid phase synthesis of phosphopeptides. International Journal of Peptide and Protein Research 34:129–133.

Perich J (1991) Synthesis of O-phosphoserine and O-phosphothreonine-containing peptides. Methods in Enzymology 201:225–233.

Poulter L, Barrat D, Scott C, Caputo C (1983) Localizations and immunoreactivities of phosphorylation sites on bovine and porcine tau proteins and a PHF-tau fragment. J Biol Chem 268:9636–9644.

Roder H, Ingram V (1991) Two novel kinases phosphorylate tau and the KSP site of heavy neurofilament subunits in high stoichiometric ratios. J Neurosci 11:3325–3343.

Schägger H and Von Jagow G (1987) Tricine-sodium dodecyl sulfate-polyacrylamide gel electrophoresis for the separation of proteins in the range of 1 to 100 kDa. Analytical Biochemistry 166:368–379.

Sturgill T, Ray L, Anderson N, Erickson A (1991) Purification of activated protein kinase from epidermal growth factor treated 3T3-L1 fibroplasts. Meth Enzymol 200:342–351.

Selden S, Pollard T (1983) Phosphorylation of microtubule-associated proteins regulates their interaction with actin filaments. J Biol Chem 258(11):7064–71.

Steiner B, Mandelkow E, Biernat J, Gustke N, Meyer H, Schmidt B, Mieskes G, Soling H, Drechsel D, Kirschner M, Goedert M, Mandelkow E (1990) Phophorylation of microtubule-associated protein tau: identification of the site for $Ca^{2+}$-calmodulin dependent kinase and relationship with tau phosphorylation in Alzheimer tangles. The EMBO J 9:3539–3544.

Studier F, Rosenberg A, Dunn J, Dubbendorf J (1990) Use of T7 RNA polymerase to direct expression of cloned genes. Methods Enzymol 185:60–89.

Towbin H, Staehelin T, Gordon J (1979) Electrophoretic transfer of proteins form polyacrylamide gels to nitrocellulose sheets: procedure and some applications. Proc Natl Acad Sci USA 76:4350–4354.

Trojanowski J, Schuck T, Schmidt M, Lee V (1989) Distribution of tau proteins in the normal human central and peripheral nervous system. J. Histochem. Cytochem. 37(2) :209–15.

Vandenheede J, Yang S, Goris J, Merievede W (1980) ATP x Mg-dependent protein phosphatase from rabbit skeletal muscle. Purification of the activating factor and its characterization as a bifunctional protein also displaying synthase kinase activity. J Biol Chem 255: 11768–11774.

Vandermeeren M, Mercken M, Vanmechelen E, Six J, Van de Voorde A, Martin J, Cras, P (1993) Detection of tau proteins in normal and Alzheimer's disease fluid with a sensitive sandwich enzyme linked assay J Neurochem 61:1828–1834.

Van de Voorde A, Vanmechelen E, Vandermeeren M, Dessaint F, Beeckman W, Cras P (1995) Detection of tau in cerebrospinal fluid. Research Advances in Alzheimer's disaese and related disorders, Ed. Ibqal, Mortimer, Winblad & Wisniewski, John Wiley & Sons Ltd.

Vulliet R, Halloran S, Braun R, Smith A, Lee, G (1992) Proline-directed phosphorylation of human tau protein. J Biol Chem 267:22570–22574.

Watanabe N, Takio K, Hasegawa M, Arai T, Titani K, Ihara Y, (1992) Tau 2: a probe for a ser conformation in the amino terminus of tau. J Neurochem 58:960–966.

Wolozin B, Davies P (1987) Alzheimer-related neuronal protein A68: specificity and distribution. Ann Neurol 22:521–526.

Wolozin B, Pruchnicki A, Dickson D, Davies P (1986) A neurological antigen in the brains of Alzheimer's patients. Science 232:648–650.

Wood J, Mirra S, Pollock N, Binder L (1986) Neurofibrillary tangles of Alzheimer's disease share antigenic determinants with the axonal mirotubule-associated protein tau. Proc Natl Acad Sci (USA) 83:4040–4043.

What is claimed is:

1. A monoclonal antibody which forms an immunological complex with a phosphorylated epitope of an antigen present in a particular subclass or form of phosphorylated tau protein without forming an immunological complex with fetal tau and without forming an immunological complex with biopsy or autopsy derived brain material from individuals suffering or having died from diseases in which neurofibrillary tangle (NFT) is not a pathological hallmark, wherein the phosphorylated epitope resides in the region spanning positions 146–251 (SEQ ID NO:1).

2. A monoclonal antibody termed AT100 secreted by the hybridoma deposited at ECACC on Apr. 21, 1994 under No.94042117.

3. A hybridoma which secretes the monoclonal antibody according to any of claims 1 or 2.

4. A process for obtaining and isolating a hybridoma secreting the monoclonal antibody according to claim 1, comprising:

(a) starting from the spleen cells of an animal previously immunized in vivo, or from spleen cells of such cells previously immunized in vitro, with an antigen selected from
   i) phosphorylated tau present in brain extracts derived from the brains of patients having died from Alzheimer's disease (AD), or,
   ii) immunoaffinity purified phosphorylated tau isolated from the brain of a patient having died from AD,
   wherein said antigen is recognized by the monoclonal antibody according to claim 1;

(b) fusing said immunized cells with myeloma cells under hybridoma-forming conditions; and, (c) selecting those hybridomas which secrete monoclonal antibodies which specifically recognize a phosphorylated epitope of a particular subclass or form of phosphorylated tau as determined by western blot or by ELISA without recognizing an epitope of biopsy or autopsy derived brain tau material from patients having died or suffering from diseases in which NFT is not a pathological hallmark; wherein the phosohorylated epitome resides in the region spanning positions 146–251 (SEQ ID NO:1).

5. The monoclonal antibody according to claim 1 obtained by a process comprising:
   (a) starting from the spleen cells of a mouse previously immunized in vivo, or from spleen cells of such cells previously immunized in vitro, with an antigen selected from
      i) phosphorylated tau extracted and purified from a human brain sample of a patient having died from Alzheimer's disease (AD), or,
      ii) immunoaffinity-purified phosphorylated tau from the brain of a patient having died from AD,
      wherein said antigen is recognized by the monoclonal antibody;
   (b) fusing said immunized spleen cells with myeloma cells under hybridoma-forming conditions,
   (c) selecting a hybridoma which secretes the monoclonal antibody; wherein said monoclonal antibody recognizes a phosphorylated epitope residing in the region spanning positions 146–251 (SEQ ID NO:1),
   (d) culturing the selected hybridoma in an appropriate medium culture; and
   (e) recovering the monoclonal antibody excreted by said selected hybridoma; or alternatively:
   (f) implanting the selected hybridoma into the peritoneum of a mouse and, when ascites has been produced by the animal,
   (g) recovering the monoclonal antibody then formed from said ascites.

6. A process for producing a monoclonal antibody from the hybridoma of claim 3, comprising:
   (a) culturing the hybridoma in an appropriate medium culture; and,
   (b) recovering the monoclonal antibody excreted by said hybridoma; or alternatively:
   (c) implanting the hybridoma into the peritoneum of a mouse, and, when ascites has been produced by the animal,
   (d) recovering the monoclonal antibody then formed from said ascites.

7. Process for in vitro detection or diagnosis of brain/neurological disease involving a particular subclass or form of phosphorylated tau protein, comprising:
   (a) contacting the monoclonal antibody according to any of claims 1 or 2, with a preparation of NFT, PHF, or a detergent-extracted brain homogenate isolated from a patient having had a disease involving phosphorylated tau under conditions suitable for producing an antigen-antibody complex; and
   (b) detecting the immunological binding of said antibody to said brain homogenate.

8. Process for aiding the detection or diagnosis in vitro of brain disease involving a particular subclass or form of phosphorylated tau protein, comprising:
   bringing a sample of CSF or of serum from a patient suspected of suffering from a neurological disorder involving NFT, or proteins or polypeptides extracted therefrom, into contact under in vitro conditions with a monoclonal antibody according to any of claims 1 or 2, with said conditions suitable for producing an antibody-antigen complex; and,
   detecting the immunological binding of said antibody to said sample of cerebrospinal fluid, or of serum, or extract thereof.

9. The process of claim 7, wherein the disease is Alzheimer's disease.

10. The process of claim 8, wherein the disease is Alzheimer's disease.

11. Process for in vitro detection or diagnosis of brain/neurological disease involving a particular subclass or form of phosphorylated tau protein, comprising:
   (a) contacting the monoclonal antibody according to any of claims 1 or 2, with a preparation of NFT, PHF, or a detergent-extracted brain homogenate isolated from a patient having a disease involving phosphorylated tau under conditions suitable for producing an antigen-antibody complex; and
   (b) detecting the immunological binding of said antibody to said brain homogenate.

12. A process for producing a monoclonal antibody of claim 1, comprising:
   culturing the hybridoma deposited at ECACC on Apr. 21, 1994 under No. 94042117 in an appropriate medium culture, and either
   (a) implanting the hybridoma into the peritoneum of a mouse, and after ascites have been produced by the mouse, recovering the monoclonal antibody from said ascites, or
   (b) recovering the monoclonal antibody from the medium culture.

13. The hybridoma of claim 3, deposited at ECACC on Apr. 21, 1994 under No. 94042117.

14. The process of claim 7, wherein the monoclonal antibody is AT100.

15. The process of claim 8, wherein the monoclonal antibody is AT100.

16. The process of claim 11, wherein the monoclonal antibody is AT100.

17. The process according to any of claims 7, 8, 11, 14, 15, or 16, wherein said detection step comprises:
   (a) contacting the antigen-antibody complex with a second antibody under suitable conditions, to form an antigen-antibody-second antibody complex; and,
   (b) subsequently contacting said antigen-antibody-second antibody complex with a marker for specific tagging or coupling with said second antibody;
   wherein the second antibody is selected from (i) a monoclonal antibody recognizing an epitope of tau protein or phosphorylated tau protein or of any tau peptide carrying an epitope, with said epitope being different from SEQ ID NO:1; (ii) a polyclonal antibody recognizing tau protein or phosphorylated tau, or (iii) a polyclonal antibody recognizing a tau peptide, with said polyclonal antibody of (ii) or (iii) forming an immunological complex with epitopes which are different from SEQ ID NO:1.

18. A diagnostic kit, comprising:
   a monoclonal antibody according to any of claims 1 or 2, and
   a buffer solution.

19. The kit of claim 18, further comprising a peptide carrying an epitope of phosphorylated tau comprising SEQ ID NO:1 for use as a standard or for competition with respect to the antigen which is sought.

* * * * *